(12) United States Patent
Brau et al.

(10) Patent No.: US 7,018,414 B2
(45) Date of Patent: Mar. 28, 2006

(54) SUPPORT DEVICE FOR VERTEBRAL FUSION

(76) Inventors: Salvador A. Brau, 1334 Westwood Blvd., Suite 1 D, Los Angeles, CA (US) 90024; Michael L. Schiffman, 8610 S. Sepulveda Blvd., Suite 101, Los Angeles, CA (US) 90045

( * ) Notice: Subject to any disclaimer, the term of this patent is extended or adjusted under 35 U.S.C. 154(b) by 37 days.

(21) Appl. No.: 10/630,198

(22) Filed: Jul. 29, 2003

(65) Prior Publication Data

US 2004/0186571 A1    Sep. 23, 2004

Related U.S. Application Data

(60) Provisional application No. 60/399,584, filed on Jul. 30, 2002.

(51) Int. Cl.
*A61F 2/44* (2006.01)
(52) U.S. Cl. .................... 623/17.11; 623/16.11
(58) Field of Classification Search ... 623/17.11–17.16
See application file for complete search history.

(56) References Cited

U.S. PATENT DOCUMENTS

| | | | |
|---|---|---|---|
| 6,210,442 B1 | 4/2001 | Wing et al. | |
| 6,395,031 B1 * | 5/2002 | Foley et al. | ............. 623/17.11 |
| 6,468,311 B1 * | 10/2002 | Boyd et al. | .............. 623/17.16 |

FOREIGN PATENT DOCUMENTS

FR    WO 98/48738    * 11/1998

* cited by examiner

*Primary Examiner*—Thomas C. Barrett
(74) *Attorney, Agent, or Firm*—Fulwider Patton LLP

(57) ABSTRACT

A support for vertebral fusion prevents subsidence and eliminates the need for posterior surgery and instrumentation. The support is constructed from cadaveric vertebrae or an implantable man-made material. One embodiment is a U-shaped metal support that rests on the apophyseal ring of the vertebrae, with the open portion of the U facing the patient's posterior. The metal support is then connected to a previously placed threaded cage or bone dowel such as that used in anterior lumbar interbody fusion (ALIF).

9 Claims, 4 Drawing Sheets

SUPPORT DEVICE FOR VERTEBRAL FUSION

CROSS-REFERENCE TO RELATED APPLICATION

This application claims the benefit of and is a continuation-in-part of Provisional Application No. 60/399,584, filed Jul. 30, 2002.

BACKGROUND OF THE INVENTION

This invention relates to the maintenance of an adequate disc height, by the prevention of subsidence, following Anterior Lumbar Interbody Fusion (ALIF), which typically uses threaded metal cages or threaded bone dowels.

Anterior Lumbar Interbody Fusion (ALIF) using threaded devices such as cages and bone dowels has been in use for over ten years. Initially, threaded cages or dowels were expected to act as a stand-alone device that would promote fusion and maintain disc height without the need for posterior surgery and instrumentation of the spine. In spite of fusion rates better than 90 percent for single level fusion and 65 percent for two-level fusion, significant subsidence has been observed on follow-up X-rays at varying times following the procedure. This subsidence, or slow insinuation of the threaded devices into the vertebral bodies, has resulted in lost disc height, which in some patients has resulted in the failure to fuse and the recurrence of often very painful symptoms.

Subsidence occurs because the threaded devices are optimally placed more posterior than anterior, where there is maximum load on the vertebral body. The threaded devices also need to be placed at opposite sides from the midline of the vertebral body. This typically results in the threaded devices being placed entirely on softer bone, which is more prone to result in subsidence. The apophyseal ring, a structure within the vertebral body, provides an area of denser, stronger bone, which would be more resistant to subsidence. This apophyseal ring, however, is found only in the very outer circumference of the vertebral body. Furthermore, the apophyseal ring is present only on the anterior and lateral aspects of the vertebral body, not on the posterior aspects, and it is typically only 1 to 2 mm thick. Most threaded devices in use today are placed inside of the apophyseal ring and fail to take advantage of its strength. ALIF and threaded cages, therefore, have been used less frequently in recent years. This has resulted in the increase of anterior-posterior fusions, or 360 degree fusions, which have actually become the "gold standard" against which other technologies are being measured for reliability and successful outcomes.

The principal disadvantage of 360 degree fusions is that the patient then needs two separate operations, either on the same day or in two separate stages. Both operations are of significant magnitude with independent, significant morbidities. There are other problems as well. Although 360 degree fusions offer almost 100 percent fusion rates, there is not 100 percent satisfaction on the part of the patients. The most frequent and important cause of patient dissatisfaction occurs because the posterior portion of the operation causes significant destabilization of the back muscles, which are essential for improved health of the patient's back. The anterior approach, especially when used with mini-open techniques, would be preferable to 360 degree fusion because the morbidity associated with it is much less. If 360 degree fusion could be avoided, there would be significant benefit to the patient in terms of reduced morbidity and faster recuperation. This, in turn, would result in earlier resumption of physical activity and return to work. In addition, there would substantial reduction in cost of treatment, since one operation would take the place of two.

No devices or surgical methods in use at the present time can overcome the various problems associated with either ALIF or 360 degree fusion. One device, described in U.S. Pat. No. 6,210,442, tries to overcome some of these problems. The device consists of a single threaded implant incorporated into a winged structure that provides lateral support. This device, however, is not designed to take advantage of the apophyseal ring and thus fails to use it as a source of stability and strength. It would be desirable if the benefits of a single, ALIF surgery could be obtained while preventing the post-operative subsidence that typically occurs after ALIF.

SUMMARY OF THE INVENTION

The present invention solves the problems encountered in ALIF and avoids the problems of 360 degree fusions, because it requires only one operation and uses an anterior approach. The invention acts as a spacer placed around the threaded devices used in ALIF. Once inserted, the invention takes advantage of the strength of the apophyseal ring of the fused vertebrae. After allowing 0.5 to 1.0 mm of subsidence on each vertebral end plate, the device then shares the load at the strongest part of the vertebral body, the apophyseal ring. Further subsidence is prevented and the successful fusion rate is increased. This makes the anterior-only approach, or ALIF, acceptable as a stand-alone construct for one or two levels of vertebral fusion, thus eliminating the need for a 360 degree fusion, with separate anterior and posterior operations.

In one preferred embodiment of the invention, a spinal fusion support for preventing subsidence in ALIF comprises a portion of boney material adapted to be placed on the apophyseal ring of a vertebrae to be fused. Preferably the boney material itself is formed from a cadaveric vertebral body and includes the apophyseal ring of the vertebrae from which it is formed.

In an another embodiment, the spinal fusion support includes a cross member and two lateral members. The lateral members are attached to the cross member and define an interior and exterior. An associated support device, such as a threaded cage or bone dowel used in ALIF, is placed at least partially interior of the spinal support of the present invention. The spinal support can be made of bone or of man-made material, such as titanium, titanium cobalt-chromium, stainless steel, plastic, or composites. The man-made cross member may be configured so that it can be adjusted to varying lengths to fit the patient's vertebrae.

In yet another embodiment, the present invention comprises a system for anterior spinal fusion that includes a first support and a second support. The first support may be a typical ALIF device, such as a threaded cage or bone dowel that generally fits inside the apophyseal ring of a vertebrae that is to be fused. The second support is placed on the apophyseal ring of the vertebrae. The second support may be made from a boney material or from a man-made material, as described above.

Another embodiment of the present invention is an improved method of ALIF which includes placing a second support on the anterior and lateral aspects of the apophyseal ring of a vertebral body after a first support has already been placed on the vertebral body during the initial part of the ALIF.

Other features and advantages of the invention will become apparent from the following detailed description, taken in conjunction with the accompanying drawings, which illustrate, by way of example, the features of the invention.

DETAILED DESCRIPTION OF THE PREFERRED EMBODIMENTS

The present invention is a novel device, system, and method designed to provide supplemental vertebral body end plate support for devices placed in the anterior lumbar region, such as threaded interbody fusion cages or bone dowels. The present invention generally contemplates two embodiments. One, an allograft, is made from an actual vertebral body. The other embodiment is fabricated from man-made materials such as metal, plastic, or composites.

Figure 1:
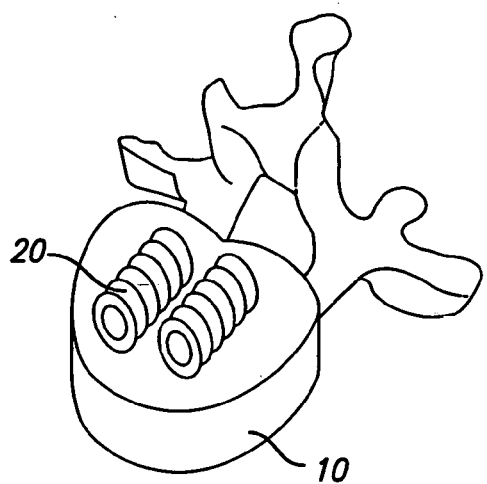
FIG. 1 is a perspective view of a typical prior art fusion device mounted on a vertebral body.
Figure 2:
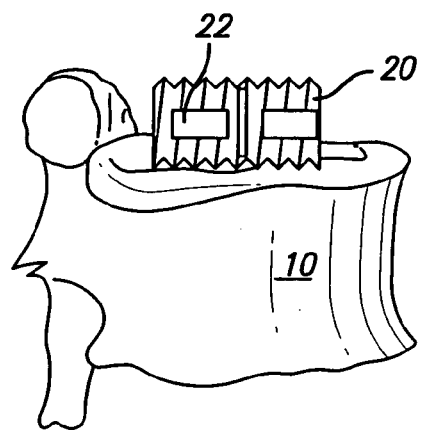
FIG. 2 is a side view of a vertebral body with a typical prior art fusion device mounted on the vertebral body.
Figure 3:
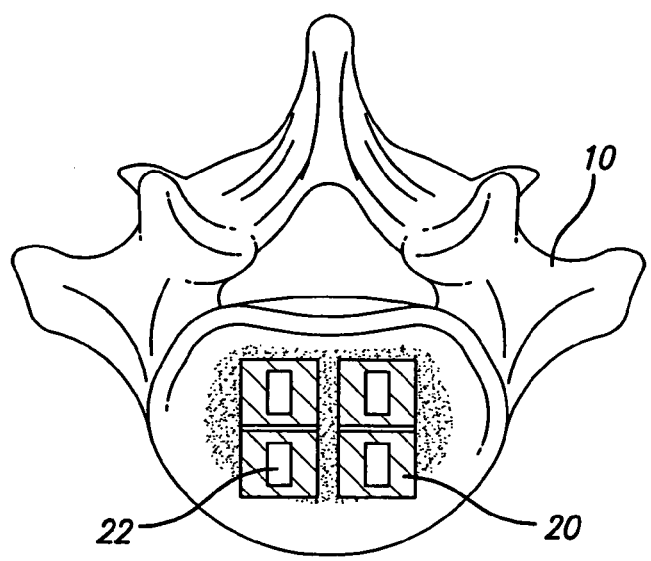
FIG. 3 is a plan view of a vertebral body with a typical prior art fusion device mounted on the vertebral body.

Preliminarily, the surgeon will effectively perform an ALIF, typically installing a first support device such as a pair of threaded cages or bone dowels. FIGS. 1, 2, and 3 depict different views of a vertebral body 10 with prior art cages 20 mounted on the vertebral body 10. Typically such cages contain open spaces 22 that permit bone growth throughout cage 20 for a stronger and more stable fusion. After the surgeon installs the cages, dowels, or other such support 20, he will then install a second support. One embodiment of the second support is an allograft. In this embodiment of the invention, the allograft will preferably be harvested from cadaveric vertebral bodies and sculpted or processed to preserve the apophyseal ring of these harvested vertebral bodies. Thus, the implanted support will have the shape of the apophyseal ring, which is generally semicircular or U-shaped, with the base of the U being the anterior part of the vertebral body where the apophyseal ring is thickest.

Figure 4:
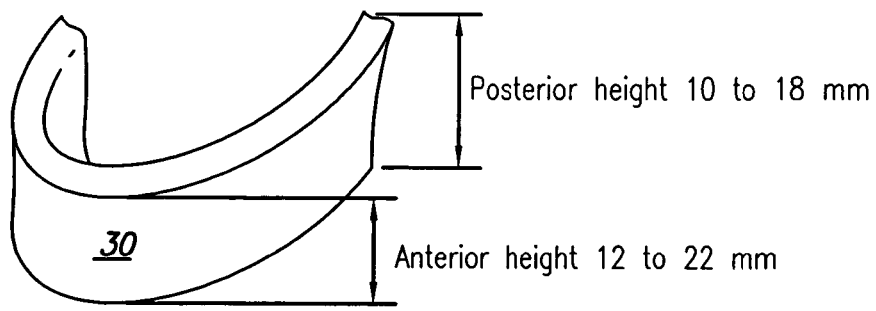
FIG. 4 is a perspective view of the allograft with typical anterior and posterior dimensions.

The allograft will be processed from differently sized cadaveric vertebral bodies to match the size of the recipient's vertebrae and to match the space available once the threaded cages 20 or similar such support are inserted into the intervertebral space. As depicted in FIG. 4, the height of the allograft, or second support 30, typically will vary between approximately 10 mm and 22 mm. It will also usually be 1 mm less than the distraction created on the vertebral end plates by the insertion of the fusion devices. This will allow a clearance of approximately 0.5 mm from each end plate to facilitate placement without fracturing the allograft.

Figure 5:
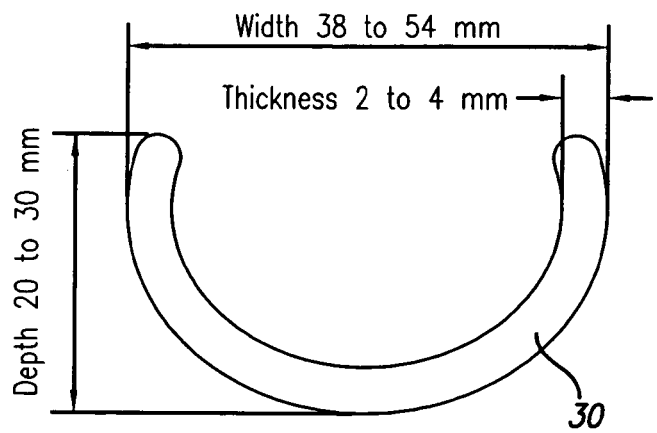
FIG. 5 is a plan view of the allograft with typical dimensions.

The allograft of the present invention can also be made in tapered heights. Such a configuration would, for example, accommodate first support 20 in the form of one or more tapered fusion cages. The anterior height of the allograft will typically be greater than the posterior height, as noted above and depicted in FIG. 4, and will range from approximately 12 mm to 22 mm. As depicted in FIG. 4, the posterior height will usually range from approximately 10 mm to 17 mm. As shown in FIG. 5, the allograft 30 will vary between approximately 20 mm and 30 mm deep and between approximately 38 mm and 54 mm wide to accommodate varying vertebral widths. The thickness of the allograft will vary between approximately 2 mm and 4 mm, depending on the amount of space remaining after the first fusion support devices are inserted.

Figure 6:
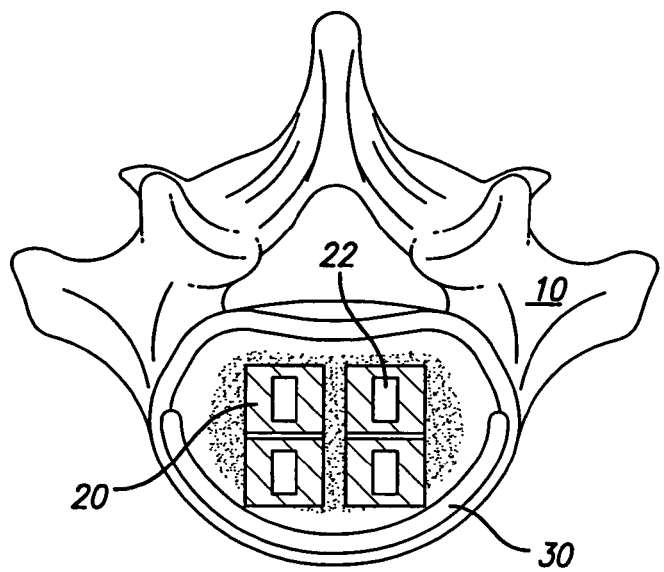
FIG. 6 is a plan view of the allograft mounted on the anterior end of the vertebral body.
Figure 7:
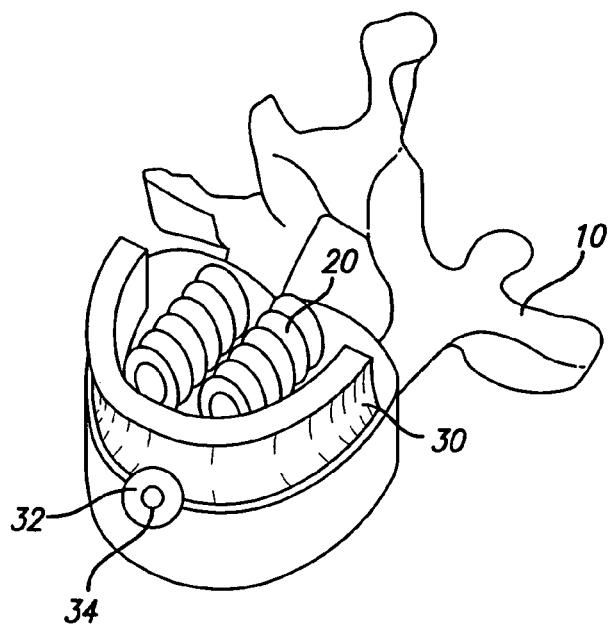
FIG. 7 is a perspective view of the allograft attached to the vertebral body.
Figure 8:
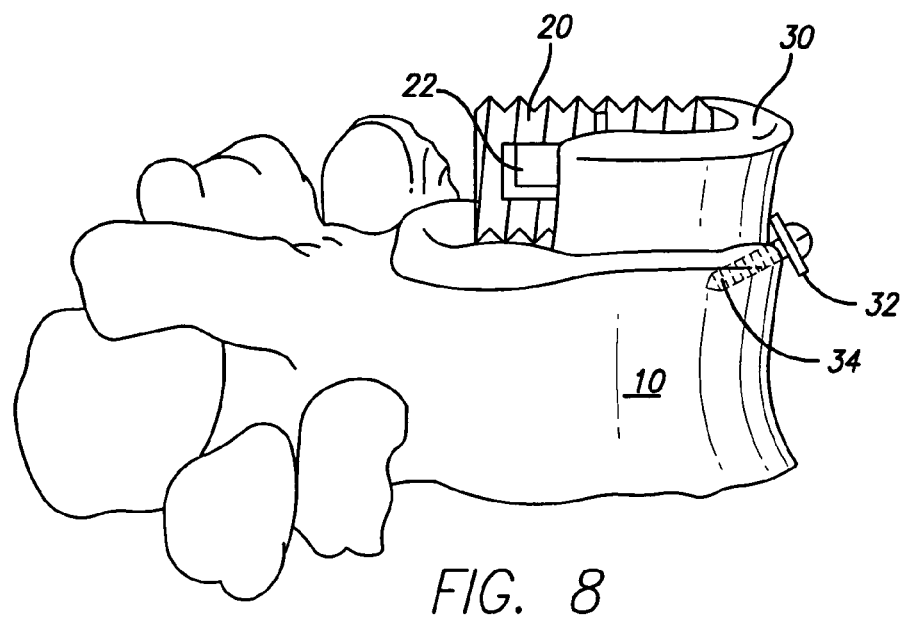
FIG. 8 is a side view of a typical prior art fusion device and an allograft placed at the anterior end of the vertebral body.

As depicted in FIG. 6, the allograft 30 will be seated at the lateral and anterior apophyseal lines of the patient's recipient vertebrae 10. This will prevent subsidence by sharing the load with the fusion devices, i.e., first support 20, with allowance for approximately 0.5 to 1.0 mm settling of these devices into the end plates. The U-shaped allograft 30 will be inserted around the already-implanted fusion devices or first support 20. Preferably the allograft 30 will be secured by a washer 32 and screw 34 that is not drilled through allograft 30. Such an arrangement is depicted in FIGS. 7 and 8. While the allograft 30 is adequate to act as a second support, there is concern that a screw hole drilled through allograft 30 may weaken it too much.

Should allograft 30 prove stout enough to accommodate one or more holes, then it can be locked into the cages 20 or vertebrae 10 by means of screws (not shown). In the case of threaded cages, the implanted allograft 30 will have two screw holes to match the ones used to attach the cages to the inserter (not shown) for implantation. Alternatively, the screw holes in the cages, dowels, or other devices can be used to attach a bracket that can then be used to hold the allograft in place and prevent it from dislodging. Those of skill in the art will recognize that the attachment of the allograft to the patient's vertebral body is a matter of choice and can vary depending on the vertebral bodies available for the allograft, the patient's physique, surgeons' techniques, and the conditions the surgeon encounters.

A second preferred embodiment of the present invention can be formed from man-made materials, such as stainless steel, titanium, plastic, or composites. The device will be seated at the lateral and anterior apophyseal lines of the recipient vertebrae and thus will prevent subsidence by sharing the load with the cages once there is approximately 0.5 to 1.0 mm of cage settling into the end plates.

Figure 9:
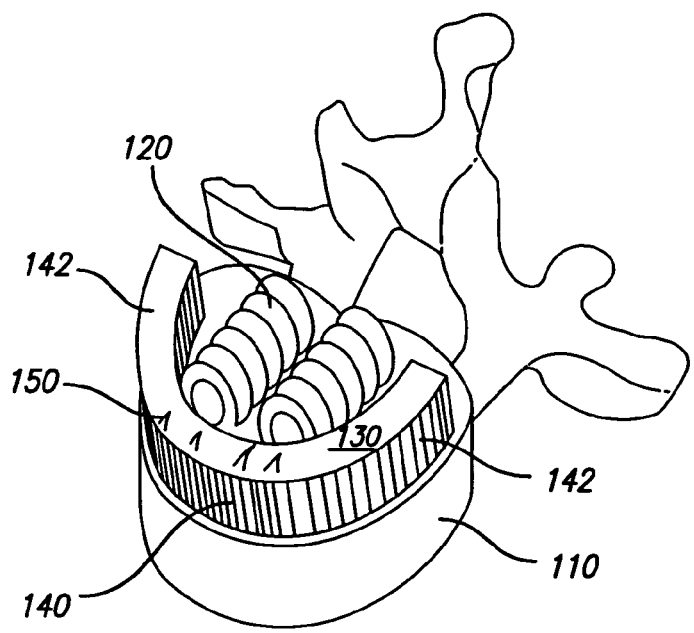
FIG. 9 is a perspective view of another embodiment of the present invention formed from man-made materials.
Figure 10:
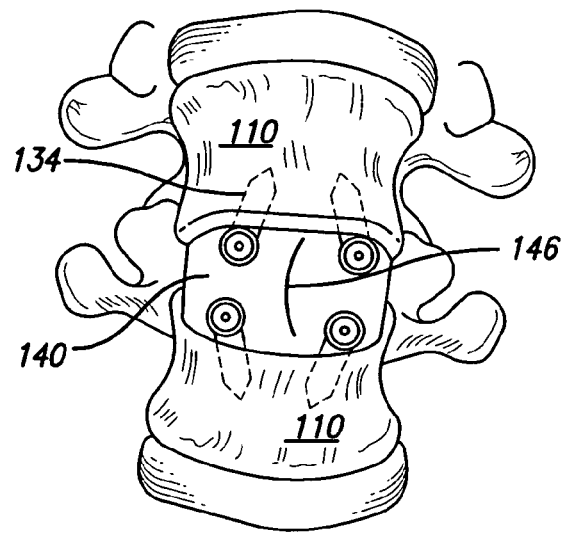
FIG. 10 is a perspective view of the of embodiment in FIG. 9, depicting the screws fastening the invention to adjacent vertebrae.
Figure 11:
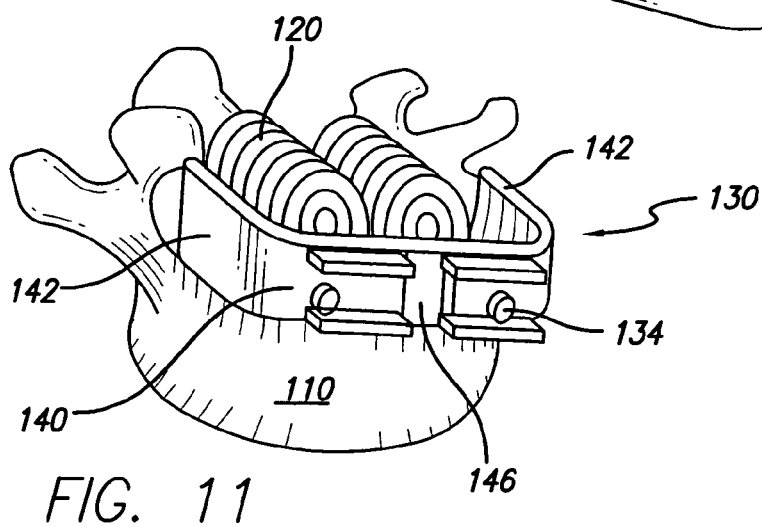
FIG. 11 is a perspective view of the invention with a slidable cross member.

In FIG. 9, the preferred embodiment is a U-shaped member 130 with an anterior cross member 140 and two lateral members 142 generally parallel to the midline of the vertebrae 110. The U-shaped member 130 will be inserted around the already-implanted first support device 120, such as cages or dowels. Anterior connecting cross member 140 will have projections 150 extending from its top and bottom edges to reach the apophyseal lines of the adjacent vertebral bodies 110. As depicted in FIGS. 10 and 11, the anterior cross member 140 will also have nests to accommodate screws 134 at the top and bottom of cross member 140. These screws 134 can be used to further secure the U-shaped member 130 to the vertebral bodies 110 above and below U-shaped member 130. The cross sectional shape of the U-shaped member is preferably that of an I-beam (not shown). The inner contour of the lateral supporting members can be threaded to match the threads and inner diameter of the cages around which the device 130 is implanted. As depicted in FIGS. 10 and 11, the cross member 140 can be made adjustable by means of a sliding assembly 146.

The height of the second support, or U-shaped member 130, will vary between approximately 10 mm and 20 mm and will be approximately 1 mm less than the distraction used on the vertebral end plates to insert the cages. This will allow a clearance of approximately 1 mm from each end plate to facilitate placement.

The depth of second support 130 will vary between approximately 20 mm to 40 mm to accommodate varying vertebral sizes. The adjustable cross member 140 will preferably be at least 55 mm wide closing to about 24 mm wide, depending on the size of the cages or dowels used. The thickness of the anterior cross member 140 and of the lateral support members 142 will preferably vary between approximately 2 mm and 3 mm, depending on the amount of space remaining once the cages are inserted.

Like the allograft 30, the man-made second support 130 can be made in a tapered height to accommodate tapered cages. The anterior height will typically range from approximately 14 mm to 21 mm. Ordinarily, the posterior height will be less than that of the anterior height, ranging from approximately 10 mm to 17 mm.

It will be noted by those of skill in the art that changes may be made to the present invention without departing from its spirit or from the scope of the claims. For example, as noted above, the device can be made of a various materials. One such preferred material is titanium cobalt-chromium, although any implantable material with adequate strength could be used. The device may also be coated with material that will foster boney in growth for more mechanical strength and stability. Others may develop first supports that are different from the traditional threaded cages and bone dowels used in ALIF. Those of skill in the art will also understand that the dimensions provided here are only approximate, and are subject to variation depending upon the available allografts, manufacturing techniques and limitations, as well as limitations created by the patient's physique and the operating technique used by the surgeon. Likewise, the description of the invention as U-shaped is quite general and should be interpreted broadly. For example, the invention could be more semicircular as shown in FIG. 5, or it could be almost circular, with perhaps 270 degrees of edge and a 90 degree opening at the posterior end. Thus, the lateral members would not in a literal sense be parallel to the patient's midline, nor would the cross member be perpendicular to the midline. As a practical matter, however, they would be. Similarly, the structure might have a fairly short cross member with lateral vertebral supports that are not exactly parallel to the patient's midline. Nevertheless, for purposes of the present invention, one should still consider the structure as U-shaped, in the sense that it is supported preferably by the anterior and lateral aspects of the apophyseal ring. In addition, how the cross member and lateral members are attached—whether they are unitary structures or welded or slidably connected—is also a matter of choice. An allograft presumably is a unitary piece of bone with a curved cross member and curved lateral members. As imaging and fabrication techniques improve, it may, for example, be possible to image and fabricate fairly rigid unitary plastic devices to conform to the precise shape of the patient's vertebrae, either before or even during the operation to fuse the vertebrae. Obviously, it is preferable that the device be supported by as much of the apophyseal ring as possible. As a practical matter, however, it is necessary that the device only be supported to the extent necessary to permanently limit or prevent subsidence. Thus, the broad scope of the invention should be understood in the context of the specification and as it is defined in the following claims.

What is claimed is:

1. A spinal fusion allograft for placement adjacent to a vertebral body having an anterior portion, two lateral portions, a posterior portion, and an apophyseal ring, comprising:
    an anterior cross member with two lateral ends,
        the cross-member generally configured in the shape of the anterior portion of the adjacent vertebral body and configured to be for transmitting force through and fusing with the adjacent vertebral body, and
        the cross member configured to between 12 and 22 millimeters high and comprised of original cadaveric bone having at least a portion of an apophyseal ring coextensive with the apophyseal ring of the adjacent vertebral body;
    two lateral members, each having an anterior end and a posterior end, the anterior end being connected to one of the lateral ends of the anterior cross member,
        each lateral member being generally configured in the shape of the adjacent lateral portion of the adjacent vertebral body and for transmitting force through and fusing with the adjacent lateral portion of the adjacent vertebral body, and,
        each lateral member being configured to between 10 and 18 millimeters high and comprised of original cadaveric bone having at least a portion of an apophyseal ring coextensive with the apophyseal ring of the adjacent vertebral body;
    wherein the posterior ends of the lateral members define a posterior opening of the allograft; and
    a connector adapted to connect the allograft to an associated support located posterior of the anterior cross member.

2. The spinal fusion allograft of claim 1, wherein the associated support is adapted to be configured in different lengths.

3. The spinal fusion allograft of claim 1, further comprising a connector adapted to connect the lateral members to an associated support located posterior of the cross member and interior of the lateral members.

4. The spinal fusion allograft of claim 2, wherein the associated supports comprise at least one of a group of materials including titanium, titanium cobalt-chromium, stainless steel, plastic, and composites.

5. The spinal fusion allograft of claim 1, wherein the cross member further comprises an inferior edge adapted to secure the cross member to the adjacent vertebral body.

6. The spinal fusion allograft of claim 5, wherein the edge is serrated.

7. The spinal fusion allograft of claim 5, wherein the lateral members further comprise an inferior edge adapted to secure the lateral member to the adjacent vertebral body.

8. The spinal fusion allograft of claim 1, wherein each posterior end of the lateral members has a width of 2 to 4 millimeters.

9. The spinal fusion allograft of claim 1, wherein the allograft has a depth of 20 to 30 millimeters.

* * * * *